United States Patent [19]

Ege

[11] Patent Number: 4,832,940

[45] Date of Patent: May 23, 1989

[54] METHOD OF LOCATING OR IMAGING ACTIVATED T-LYMPHOCYTES WITH A TARGETING POLYPEPTIDE

[75] Inventor: Thorfinn Ege, Tranby, Norway

[73] Assignee: Nycomed AS, Oslo, Norway

[21] Appl. No.: 921,061

[22] Filed: Oct. 21, 1986

[30] Foreign Application Priority Data

Oct. 22, 1985 [GB] United Kingdom ................ 8525974

[51] Int. Cl.$^4$ .................... A61K 49/00; A61K 49/02; A61K 49/04
[52] U.S. Cl. ........................................ 424/1.1; 424/4; 424/5; 424/7.1
[58] Field of Search ......................... 424/1.1, 4, 7.1, 9, 424/5; 436/506, 512, 804; 530/387, 388, 399

[56] References Cited

U.S. PATENT DOCUMENTS

| | | | |
|---|---|---|---|
| 4,443,427 | 4/1984 | Reinherz et al. | 424/1.1 |
| 4,454,106 | 6/1984 | Gansow et al. | 424/1.1 |
| 4,472,371 | 9/1984 | Burchiel et al. | 424/1.1 |
| 4,473,493 | 9/1984 | Gillis | 260/112 R |
| 4,550,086 | 10/1985 | Reinherz et al. | 436/506 |
| 4,578,335 | 3/1986 | Urdal et al. | 435/68 |
| 4,634,586 | 1/1987 | Goodwin et al. | 424/1.1 |
| 4,695,538 | 9/1987 | Cote et al. | 424/1.1 |

FOREIGN PATENT DOCUMENTS

| | | | |
|---|---|---|---|
| 0149709 | 7/1985 | European Pat. Off. | 424/1.1 |
| 0173629 | 3/1986 | European Pat. Off. | |
| WO-8102522 | 9/1981 | PCT Int'l Appl. | 424/1.1 |

OTHER PUBLICATIONS

Gaulton et al: Clin. Immunol. Immunopathol. 36, (1985), 18 et seq.
Robb et al: J. Exp. Med. 154 (1981) 1455.
Bradwell et al: Immunol. Today, 6 (1985) 163 et seq.
Magnetic Resonance Imaging, 3 (1985) 73.
Robb: J. Immunol. Methods 81 (1985) 15.
Biotechnology, vol. 3, No. 10, Oct. 1985, pp. 889, 890, 892, 894, New York Rodwell "Linker technology: Antibody-mediated delivery systems".
Chemical Abstracts, vol. 103, No. 13, Sep. 30, 1985, p. 477, "Identification of Interleukin-2 producer and responder T lymphocyte subpopulations by immunoperoxidase staining".

Primary Examiner—John F. Terapane
Assistant Examiner—J. E. Thomas
Attorney, Agent, or Firm—Bacon & Thomas

[57] ABSTRACT

The present invention provides targeting polypeptides for use in targeting and identifying activated T-lymphocytes in the human or animal body, the targeting polypeptides being capable of binding specifically to the interleukin-2 receptors of activated T-lymphocytes or to molecules associated with the receptors and carrying one or more physiologically compatible imaging agents. Such targeting polypeptides can be used for, example, in the location of tumours and abscesses and other inflammatory conditions and in the monitoring of tissue transplants for possible rejection.

10 Claims, No Drawings

METHOD OF LOCATING OR IMAGING ACTIVATED T-LYMPHOCYTES WITH A TARGETING POLYPEPTIDE

The present invention concerns biological macromolecules for use in targeting and identifying activated T-lymphocytes.

T-lymphocytes constitute an important part of the immune defense against both foreign cells (parasites and grafts or transplants) and abnormally altered endogenous cells (tumours). Dormant T-lymphocytes (T-cells) recognizing a non-self structure on such cells will respond by proliferation and activation, thereby amplifying the number of cells capable of recognizing and reacting against these structures.

The activated T-lymphocytes accumulate in the region of the activating structures and thus identification of the location of activated T-lymphocytes in an organism is capable of providing a means of locating, for example, tumours and abscesses, and also of monitoring the immune response against tissue transplants (allografts).

One possible way of identifying the location of activated T-cells is to target an imaging agent e.g. a contrast giving agent or a radio-nuclide, to such cells. Potential targeting vehicles are molecules that interact with activated T-cells but with substantially no other cells. One structure that seems to be specific to activated T-cells is the interleukin-2 receptor that appears on these cells during their proliferative response. Molecules that bind specifically to this receptor, or to receptor-associated molecules, can be used as targeting vehicles in this context. As activated T-lymphocytes are known in vitro to bind both antibodies reacting with the interleukin-2 receptor, and also the hormone itself, it is possible to use in vivo the hormone and cell binding fragments thereof and antibodies or fragments thereof binding to the hormone receptor as targeting vehicles, when attached to a suitable imaging agent to identify the location of activated T-cells.

The present invention therefore provides, targeting polypeptides for use in targeting and identifying activated T-lymphocytes in the human or animal body, said targeting polypeptides being capable of binding specifically to the interleukin-2 receptors of activated T-lymphocytes or to molecules associated with said receptors and carrying one or more physiologically compatible imaging agents. The above targeting polypeptides include, in particular, interleukin-2 iself, also including derivatives and fragments thereof, and antibodies against the said receptors and receptor-associated molecules as well as fragments of these antibodies capable of binding specifically with said receptors or receptor associated molecules.

The term 'imaging agent' as used herein includes atoms or groups capable of giving signals which can be used in diagnostic imaging in vivo.

The targeting polypeptide may be part of a sandwich system in which a second polypeptide carrying an signal-giving atom or group is bound to the targeting polypeptide. In such a system, the said second polypeptide with the said signal-giving atom or group may be regarded as the physiologically compatible imaging agent carried by the targeting polypeptide.

In general, the targeting polypeptide is preferably capable of binding directly to the said interleukin-2 receptors.

The receptor associated molecule may be a polypeptide naturally attached to the interleukin-2 receptors of activated T-lymphocytes or it may be an exogenous polypeptide, capable of binding specifically to said receptors, such as an antibody introduced for the purpose of diagnostic location according to the invention, for example in a sandwich system. Such an exogenous polypeptide may be attached directly to the interleukin-2 receptor or may be associated via a naturally occurring attached polypeptide as described above.

Imaging agents include, for example, radio-nuclides, such as Tc-99m and contrast agents, for example X-ray contrast agents such as the many iodine containing molecules used in conventional X-ray imaging, or NMR imaging agents such as paramagnetic or ferromagnetic substances.

In general, non-invasive location or imaging of the site of the concentrations of activated T-cells is preferred and the imaging agents of the types mentioned above will normally permit this, if capable of providing a signal of suitable strength for diagnostic imaging.

The imaging agent may be attached to the targeting polypeptide in any convenient way, provided the site of attachment does not interfere with the binding reaction. Methods of coupling proteins and polypeptides to active molecules are well known in the art. In general, a coupling agent will be used which is capable of reacting with functional groups on both the targeting polypeptide and the imaging agent.

Suitable radionucleides include, in addition to Tc-99m, In-111, I-123 and I-131. Tritium (H-3) is not however included due to its low signal giving capability which is insufficient for diagnostic imaging. Various labelling methods with radioactive isotopes of iodine have been known for many years, as from the publication of Fraker PJ and Speck JC in Biochem. Biophys. Res. Comm. 80, 849 (1978) or Millar WI and Smith JF in Int. J. Appl. Rad. Isot. 34, 639 (1983). Also technetium-99m may be chemically bound directly to the polypeptides as exemplified by D. W. Wong and co-workers in The Journal of Nuclear Medicine 23: 229–234,m (1982). Alternatively, bifunctional chelating agents such as diethylenetriaminepentaacetic acid may be used as a coupling agent between the polypeptides and Tc-99m, as exemplified by Ban-An Khaw and coworkers in Hybridoma 3: 11–21, 1984. When bifunctional chelating agents are used, other cationic radionucleides can be used in the place of Tc-99m, ie. In-111, by simly adding In-111-chloride to the conjugates of the polypeptides and the bifunctional chelating agents.

Suitable X-ray contrast agents include, in particular, ionic and non-ionic iodo-benzene contrast agents such as those described in United Kingdom Pat. Nos. 973881, 1321591 and 1548594. Most of such contrast agents are derived from iodinated benzoic and isophthalic acids and the acid halides of such acids can readily be used to form amidelinkages to the polypeptides.

Suitable NMR imaging agents include, in particular paramagnetic ions such as $Co^{2+}$, $Mn^{2+}$, $Cu^{2+}$, $Cr^{3+}$, $Fe^{2+}$, $Fe^{3+}$, $Eu^{3+}$, $Gd^{3+}$, $Gd^{3+}$, $Dy^{3+}$ or $Ho^{3+}$. These will advantageously form part of suitably attached chelating molecule for example ethylene diamine tetraacetic acid or related molecules such as are described in European Patent Application No. 85303757.0 which describes techniques which are capable of attaching such molecules to targeting polypeptides. NMR imaging agents also include ferromagnetic particles, e.g. particles comprising a ferromagnetic substance advantageously contained in a biodegradable substance such as a polysaccharide or protein.

The invention also extends to the use of the targeting polypeptides in the location or imaging of concentrations of T-cells, in particular in the location of tumours and abscesses and other inflammatory conditions and in the monitoring of tissue transplants for possible rejection. The substance will normally be given by injection, e.g. intravenously, for example in solution or suspension in a physiologically compatible solution for injection such as physiological saline.

Thus, the invention includes a method of locating or imaging activated T-lymphocytes wherein a targeting polypeptide carrying one or more physiologically compatible imaging agents which is capable of binding to the interleukin-2 receptors of activated T-lymphocytes or to molecules associated with said receptors is administered to the subject and the position of said imaging agent(s) in said subject is located.

As indicated above, the targeting polypeptide may bind directly to the said receptor (or natural receptor associated molecule) or a first polypeptide binding with said receptor (e.g. an antibody) may be administered to provide an exogenous receptor associated molecule and the targeting polypeptide will then bind specifically to said first polypeptide.

According to a still further feature of the invention we provide imaging compositions comprising a targeting polypeptide according to the invention together with one or more pharmaceutical excipients or carriers. The compositions will normally be administered by injection and will thus comprise the targeting polypeptide in solution in an injectable liquid, for example physiological saline.

The following non-limiting Example is intended to illustrate the present invention.

EXAMPLE

1. Human, defibrinated peripheral blood was mixed with an equal volume of 0.9% NaCl, and layered on top of separation medium (lymphoprep from Nycomed AS, Norway) in a centrifuge tube. After centrifugation at 800g for 20 minutes in a swing-out rotor, lymphocytes were isolated from the plasma-Lymphoprep interface. The white cells were washed 3 times in 0.9% sodium chloride and resuspended to a final concentration of $50 \times 10^6$ cells per ml.

2. A mouse monoclonal antibody recognizing the rat Il-2 receptor (Clinical Experimental Immunology 59 (1985)37–44) was purified from mouse ascites fluid with the aid of Affi-Gel protein A from Bio-Rad. The ascites fluid was diluted with an equal volume of binding buffer (Bio-Rad) and filtered. The filtered ascites fluid was applied to a 2 ml Affi-Gel protein A column, and the IgG fraction eluted at pH 5.5. The fraction of the eluate to be used as intact immunoglobulin was dialyzed against phosphate-buffered saline, pH 7.0 and stored at +4° C. until used.

The fraction of immunoglobulins to be used as immunoglobulin F(ab)'2 fragments was dialyzed against acetate buffer pH 4.5 overnight. 4 mg IgG in 4 ml were mixed with 140 μl pepsin (lmg per ml) and incubated at 37° C. for eight hours. 1 ml Tris-buffer pH 9.0 was then added to stop the reaction and the mixture dialyzed against 20mM Tris pH 7.6 for 12 hours. F(ab)'2 fragments were purified from undigested IgG on a mono Q column using Pharmacia's FPLC by continuous Nacl gradient. The F(ab)'2 fraction was stored at +4° C. until used.

3. Il-2 labelled with $I^{125}$ was obtained from New England Nuclear.

4. IgG and F(ab)'2 reacting with the Il-2 receptor of rats were iodinated by the Iodogen method: 0.1 mg Iodogen (Pierce) was dissolved in 1 ml chloroform, and 20 μl aliquots added to polypropylene centrifuge tubes and evaporated to dryness. To iodinate proteins, 50 μl borate buffer, pH 8.4, 10 μg protein (in 10 μl) and 1 mCi $Na^{125}I$ were added to the Iodogen-tubes. The reaction was allowed to proced for 10 min at 0° C., and then stopped by diluting the reagents to 500 μl in phosphate buffered saline, pH 7.0. The labelled proteins were then searated from unincorporated iodine by gel filtration on a G-25 Sepharose column.

5. To induce a host-versus-graft response localized to the poplietal lymph node in Wistar outbred rats, 50 μl of human peripheral lymphocytes prepared as in (1) above were injected into the right rear footpad of the rats.

6. To analyse specific accumulation of labelled IgG or F(ab)'2 or Il-2 reacting with the Il-2 receptor at sites of activated T cells, 0.1 ml of phosphate buffered saline containing 3.5–7μl of $^{125}I$ labelled proteins were injected intravenously into the rats. At various time points after injection, the rats were killed and the radioactivity in various organs determined.

Results

A much higher accumulation of labelled Il-2 and antibodies/antibody fragments was observed in the lymph node undergoing host versus graft rejection compared with the contralateral poplietal lymph node, and also when compared with other organs. The highest tissue/blood ratio for the different iodinated proteins occurred at different times after injection.

I claim:

1. A method for locating or imaging a region containing an in vivo accumulation of activated T-lymphocytes in a subject, which comprises administering to a subject an effective amount, for locating or imaging, of a targeting polypeptide capable of binding specifically to interleukin-2 receptors of activated T-lymphocytes and carrying one or more physiologically compatible imaging agents, to bind said targeting polypeptide in vivo to interleukin-2 receptors of activated T-lymphocytes in a region containing an accumulation of said activated T-lymphocytes to locate or image said accumulation of activated T-lymphocytes, said method excluding introduction of an antibody to clear nonlocalized targeting polypeptides.

2. A method as claimed in claim 1 in which the targeting polypeptide comprises interleukin-2.

3. A method as claimed in claim 1 in which the targeting polypeptide comprises an antibody capable of binding specifically to the interleukin-2 receptors of activated T-lymphocytes.

4. A method as claimed in claim 1 in which the targeting polypeptide is a combination of a first polypeptide capable of binding directly to the interleukin-2 receptors of activated T-lymphocytes and a second polypeptide bound to said first polypeptide, said second polypeptide having bound thereto one or more physiologically compatible imaging agents.

5. A method as claimed in claim 1 in which the targeting polypeptide carries one or more imaging agents selected from the group consisting of radionuclides, x-ray contrast agents, and NMR imaging agents.

6. A method as claimed in claim 1 in which the targeting polypeptide carries one or more imaging agents selected from the group consisting of Tc-99m, In-111, I-123 and I-131, ionic and non-ionic iodo-benzene x-ray contrast agents and paramagnetic ion NMR contrast agents.

7. A method according to claim 1 wherein the region of activated T-lymphocytes is caused by a tumor.

8. A method as claimed in claim 1 wherein the region of activated T-lymphocytes is caused by an abscess.

9. A method as claimed in claim 1 wherein the region of activated T-lymphocytes is caused by an inflammatory condition.

10. A method as claimed in claim 1 in which the region of activted T-lymphocytes is caused by tissue transplant rejection.

* * * * *